US009320868B2

(12) United States Patent
McHugh

(10) Patent No.: US 9,320,868 B2
(45) Date of Patent: Apr. 26, 2016

(54) CATHETER AND A METHOD FOR MANUFACTURING A CATHETER

(75) Inventor: Adrian McHugh, Kilcolgen (IE)

(73) Assignee: Flip Technologies Limited, Dangan, Galway (IE)

( * ) Notice: Subject to any disclaimer, the term of this patent is extended or adjusted under 35 U.S.C. 154(b) by 816 days.

(21) Appl. No.: 13/637,056

(22) PCT Filed: Mar. 28, 2011

(86) PCT No.: PCT/IE2011/000020
§ 371 (c)(1),
(2), (4) Date: Dec. 4, 2012

(87) PCT Pub. No.: WO2011/117852
PCT Pub. Date: Sep. 29, 2011

(65) Prior Publication Data
US 2013/0090599 A1    Apr. 11, 2013

(30) Foreign Application Priority Data
Mar. 26, 2010    (IE) .................................. S2010/0181

(51) Int. Cl.
| | |
|---|---|
| *A61M 25/16* | (2006.01) |
| *A61M 25/00* | (2006.01) |
| *A61B 18/14* | (2006.01) |
| *A61M 25/10* | (2013.01) |
| *H05B 3/10* | (2006.01) |
| *H05K 1/02* | (2006.01) |
| *A61B 18/08* | (2006.01) |
| *A61B 18/00* | (2006.01) |

(52) U.S. Cl.
CPC ........ *A61M 25/0009* (2013.01); *A61B 18/1492* (2013.01); *A61M 25/0043* (2013.01); *A61M 25/0068* (2013.01); *A61M 25/10* (2013.01); *H05B 3/10* (2013.01); *H05K 1/028* (2013.01); *A61B 18/08* (2013.01); *A61B 2018/00214* (2013.01); *A61M 25/0082* (2013.01); *A61M 2025/0096* (2013.01); *Y10T 29/49155* (2015.01)

(58) Field of Classification Search
CPC ..................... A61M 25/0009; A61M 25/0043; A61M 2025/0166; A61M 25/10184
See application file for complete search history.

(56) References Cited

U.S. PATENT DOCUMENTS

| | | |
|---|---|---|
| 3,568,660 A | 3/1971 | Crites et al. |
| 5,855,552 A | 1/1999 | Houser et al. |
| 5,991,650 A | 11/1999 | Swanson et al. |
| 2002/0087208 A1 | 7/2002 | Koblish et al. |

FOREIGN PATENT DOCUMENTS

WO    2009001327 A2    12/2008

OTHER PUBLICATIONS

International Search Report with Written Opinion for PCT/IE2011/000020 dated Aug. 2, 2011.

*Primary Examiner* — Aarti B Berdichevsky
(74) *Attorney, Agent, or Firm* — Sughrue Mion, PLLC

(57) ABSTRACT

A balloon catheter comprising a catheter (3) and a balloon (7) located at a distal end (5) of the catheter (3). A plurality of measuring electrodes (12) formed on a primary substrate (17) extend around the catheter (3) within the balloon (7). The primary substrate (17) is formed by a portion of a flexible resilient membrane (25) which also forms a secondary substrate (19). The measuring electrodes (12) are formed on the primary substrate (17) by first electrically conductive tracks (27) and second electrically conductive tracks (28) which are electrically connected to the first electrically conductive tracks (27) are simultaneously formed on the secondary substrate (19). The membrane (25) is coiled to form a roll, and the primary substrate (17) is also coiled around the rolled secondary substrate (19). The coiled primary and secondary substrates (17,19) is urged through a second lumen (20) in the catheter (3) from the proximal end (4) thereof to a radial slot (21) in the catheter communicating with the second lumen (20). The primary substrate (17) is urged through the radial slot (20) and wrapped around and bonded to the catheter (3) to form the measuring electrodes (12) as band electrodes.

17 Claims, 4 Drawing Sheets

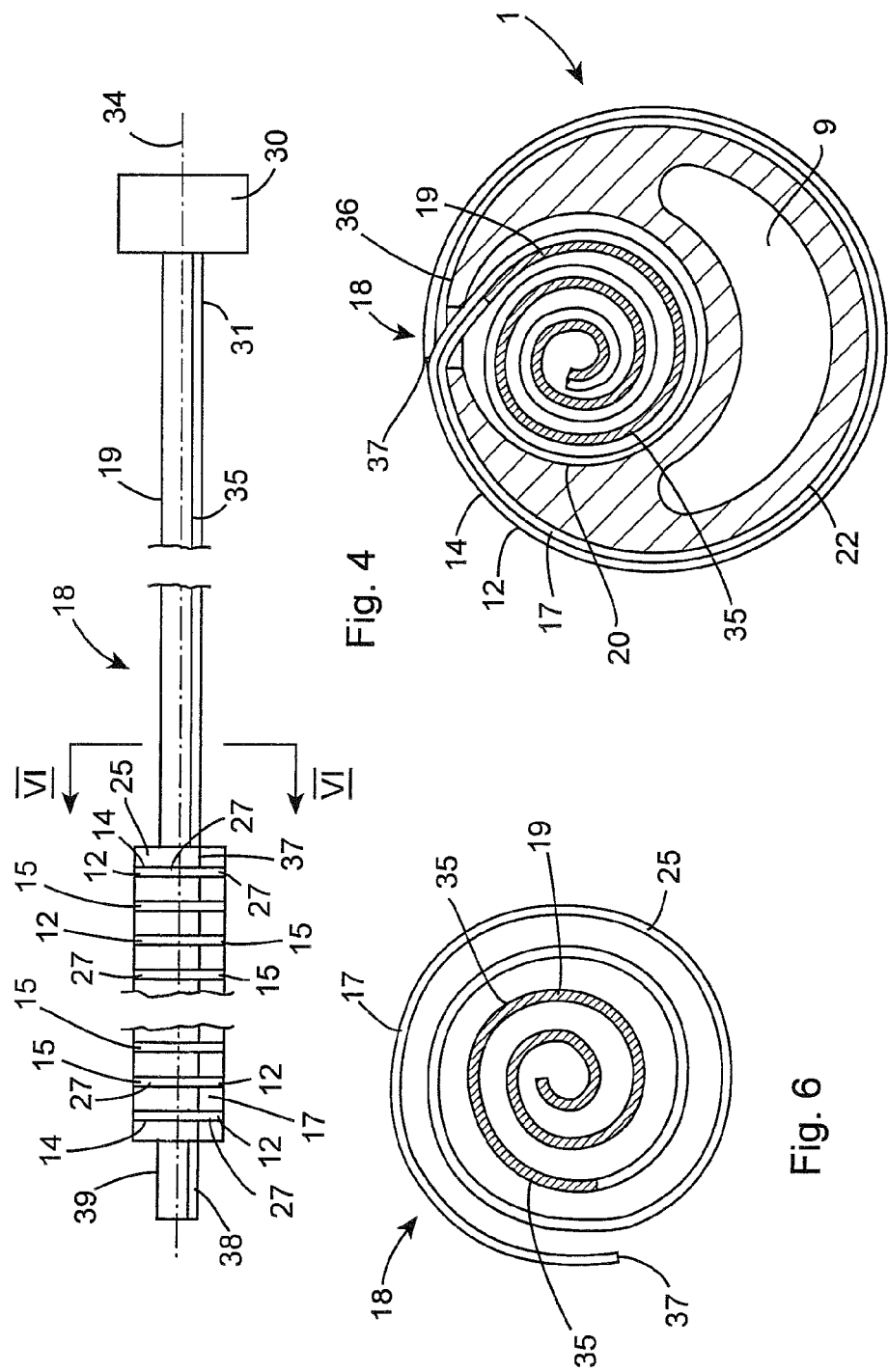

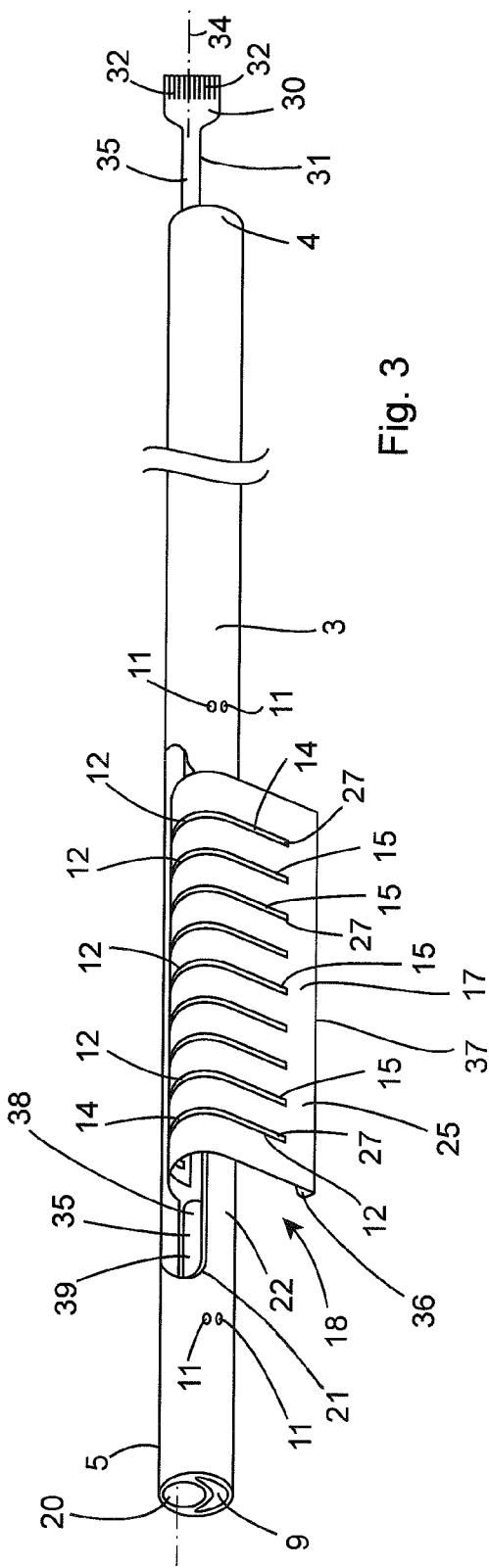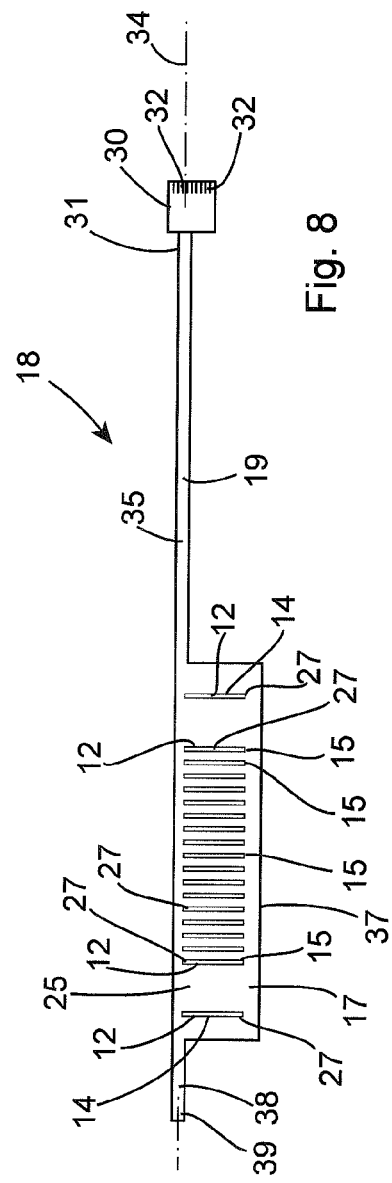

CATHETER AND A METHOD FOR MANUFACTURING A CATHETER

BACKGROUND OF THE INVENTION

The present invention relates to a catheter, and to a method for manufacturing a catheter, for example, a catheter with one or more electrodes or a heating element formed on a surface thereof. The invention also relates to an assembly for use in the manufacture of a catheter.

Catheters having one or more electrodes formed on a surface thereof or a heating element formed on a surface thereof are known. Such catheters may be plain catheters, or balloon catheters. Catheters which are provided with electrodes formed on an outer surface thereof are typically provided to facilitate measuring of a transverse cross-sectional dimension or a volume of a vessel or lumen in which the catheter is located in a human or animal body, such as a blood vessel, a cavity of the heart, the stomach, the urethra, the oesophagus, the intestine, and other such vessels, lumens and organs. Alternatively, the electrodes may be provided for facilitating ablating of tissue in a vessel or lumen by passing an electric current or a high frequency signal through the tissue from one electrode to another. Where such catheters are provided with a heating element, the heating element may be used also for ablating tissue by heating.

In general, where such catheters, either balloon catheters or plain catheters, are provided with electrodes for measuring a transverse cross-sectional dimension or the volume of a vessel or lumen, the electrodes typically are located at a distal end of the catheter in spaced apart relationship relative to each other, and typically, are formed by band electrodes extending around the catheter. The two outermost electrodes are provided as stimulating electrodes to which a stimulating electric current is applied, and the electrodes located between the outermost electrodes are sensing electrodes on which a voltage response signal is developed when the stimulating electric current is applied to the stimulating electrodes, and the catheter is located in the vessel with an electrically conductive medium present in the vessel. The voltage response signals developed on the sensing electrodes are indicative of an adjacent transverse cross-sectional dimension of the vessel or lumen. Alternatively, when the catheter is provided in the form of a balloon catheter, the electrodes are located on the catheter within the balloon, and the balloon is inflated with an electrically conductive medium. The voltage response signals developed on the sensing electrodes in response to an electric current signal applied to the stimulating electrodes are indicative of an adjacent transverse cross-sectional dimension of the balloon. Such catheters, be they plain catheters or balloon catheters, will be known to those skilled in the art.

Catheters which are provided for ablating tissue in a vessel, lumen or organ of a human or animal body ablate the tissue by applying an electric current through the tissue or subjecting the tissue to a high frequency current signal. In general, such catheters are of similar construction to those for measuring a transverse cross-sectional dimension or volume of a vessel or lumen. In the case of catheters which are provided with a heating element, the heating element, in general, is provided by an electrically resistive track which is formed towards the distal end of the catheter. By passing an electric current through the electrically resistive track, heat is generated.

In all such catheters, be they balloon catheters or plain catheters, or be they of the type for measuring a transverse cross-sectional dimension of a vessel or lumen, or for ablating tissue in a vessel or a lumen, are provided with electrodes or a heating element or heating elements on an outer surface of the catheter. The electrodes or heating elements must be coupled to corresponding ones or pairs of mutually electrically insulated electrically conductive wires, which in general extend through a lumen of the catheter from the electrodes or heating elements to the proximal end of the catheter for coupling to suitable electronic control and analytical equipment.

The manufacture of such catheters, be they balloon catheters or plain catheters, is quite a complex, tedious and time consuming task. Firstly, the electrodes or heating elements must be secured to the outer surface of the catheter, which is a tedious and time consuming task. Secondly, the electrically conductive wires which are to be coupled to the electrodes or heating elements must first be passed through a lumen in the catheter from the proximal end thereof, and urged through one or more radially extending openings from the lumen adjacent the electrodes or heating elements. The wires must then be electrically connected by either soldering or by an electrically conductive adhesive to the corresponding electrodes or heating elements. This is also a tedious and time consuming task, and there is also the risk of the wires being coupled to the incorrect ones of the electrodes or heating elements.

There is therefore a need for a method for manufacturing a catheter which addresses the problem of producing catheters known heretofore, be it a plain catheter or a balloon catheter.

The present invention is directed towards providing such a method, and the invention is also directed towards providing a catheter and a balloon catheter. The invention is also directed towards an assembly for use in the manufacture of a catheter.

SUMMARY OF THE INVENTION

According to the invention there is provided a method for manufacturing a catheter, the method comprising providing a primary substrate having at least one first electrically conductive element located thereon on an elongated carrier means, locating the carrier means in a lumen of a catheter with the primary substrate extending from the carrier means through a radial opening from the lumen with the at least one first electrically conductive element exposed exteriorly of the catheter.

Preferably, the primary substrate is secured on an outer surface of the catheter. Advantageously, the primary substrate is secured on the catheter adjacent the radial opening. Ideally, the primary substrate is secured to the outer surface of the catheter.

In one embodiment of the invention the primary substrate is secured to the outer surface of the catheter by bonding. Preferably, the primary substrate is bonded to the outer surface of the catheter by an adhesive.

In one aspect of the invention the primary substrate extends at least partially around the catheter, and preferably, the at least one first electrically conductive element is configured on the primary substrate to extend with the primary substrate at least partially around the catheter.

In another aspect of the invention the primary substrate extends completely around the catheter, and preferably, the at least one first electrically conductive element is configured on the primary substrate to extend with the primary substrate completely around the catheter.

In one embodiment of the invention the primary substrate is of a flexible material, and preferably, the at least one first electrically conductive element is flexible, and flexes with the primary substrate.

In one aspect of the invention the primary substrate is of a resilient material.

In another aspect of the invention the primary substrate is pre-tensioned to coil inwardly.

In a further aspect of the invention the primary substrate is pre-tensioned to wrap around the catheter.

Preferably, the primary substrate is located adjacent a distal end of the carrier means.

In one embodiment of the invention the carrier means is located in the lumen by urging the carrier means through the lumen until the primary substrate is located adjacent the radial opening, and the primary substrate is urged through the radial opening from the lumen. Preferably, the primary substrate is wrapped around the carrier means prior to urging the carrier means into the lumen. Advantageously, the carrier means is urged into the lumen with the primary substrate wrapped around the carrier means.

In one aspect of the invention the primary substrate is unwound from the carrier means as the primary substrate is being urged through the radial opening in the catheter. Preferably, the primary substrate is wrapped around the catheter as it is being unwound from the carrier means. Advantageously, the primary substrate is unwound from the carrier means by rotating the carrier means in the lumen.

In one embodiment of the invention the carrier means is urged into the lumen from a proximal end thereof.

In an alternative embodiment of the invention the carrier means is located in the lumen by urging the carrier means into the lumen through the radial opening until the carrier means is located in the lumen with the primary substrate extending from the carrier means through the radial opening from the lumen.

In one aspect of the invention the at least one first electrically conductive element is formed by an electrically conductive track formed on the primary substrate. Preferably, the at least one first electrically conductive element is formed on the primary substrate by one of a printing process, a deposition process and an etching process.

In another aspect of the invention the primary substrate comprises a membrane, and preferably, the primary substrate is of an electrically insulating material.

In another aspect of the invention a plurality of first electrically conductive elements are provided on the primary substrate. Preferably, the first electrically conductive elements are spaced apart and mutually electrically insulated from each other.

In one embodiment of the invention the carrier means comprises at least one second electrically conductive element electrically connected to a corresponding one of the at least one first electrically conductive element on the primary substrate.

In one aspect of the invention the carrier means comprises a secondary substrate, and the at least one second electrically conductive element is formed by an electrically conductive track extending longitudinally along the secondary substrate. Preferably, the electrically conductive track of the at least one second electrically conductive element is formed on the secondary substrate by one of a printing process, a deposition process and an etching process.

In one aspect of the invention the secondary substrate is of a flexible material.

In another aspect of the invention the secondary substrate is of a resilient material.

In a further aspect of the invention the secondary substrate comprises an elongated substrate defining an elongated longitudinally extending central axis.

In another aspect of the invention the secondary substrate is of a resilient material and is coiled about the central axis to form an elongated roll.

In a further aspect of the invention the secondary substrate is pre-tensioned to coil around the central axis.

In one embodiment of the invention the secondary substrate comprises a membrane. Preferably, the secondary substrate is of an electrically insulating material.

In one aspect of the invention the primary and secondary substrates are of similar material. Preferably, the primary and secondary substrates are integrally formed in one piece from the same sheet of material. Advantageously, the first and second electrically conductive elements are simultaneously formed on the primary and secondary substrates.

In one embodiment of the invention a plurality of the second electrically conductive elements are provided on the secondary substrate, the second electrically conductive elements being electrically insulated from each other, and being electrically connected to corresponding ones of the first electrically conductive elements.

In an alternative embodiment of the invention the at least one second electrically conductive element comprises at least one elongated electrically conductive wire. Preferably, the carrier means comprises a plurality of elongated electrically conductive wires formed into a loom, the electrically conductive wires being electrically connected to the corresponding ones of the first electrically conductive elements on the primary substrate. Advantageously, each electrically conductive wire of the carrier means is electrically connected to the corresponding first electrically conductive element by wire bonding.

In one aspect of the invention an electrical connector is located adjacent the proximal end of the carrier means, and each second electrically conductive element terminates in the electrical connector.

In another aspect of the invention the primary substrate is located on the catheter adjacent the distal end thereof.

In one aspect of the invention each first electrically conductive element forms an electrode.

In another aspect of the invention each first electrically conductive element comprises an electrically resistive heating element.

The invention also provides an assembly for use in the manufacture of a catheter, the assembly comprising an elongated carrier means, and a primary substrate having at least one first electrically conductive element located thereon, the primary substrate being provided on the carrier means.

In one aspect of the invention the carrier means is adapted for locating in an elongated lumen of a catheter with the primary substrate located adjacent a radial opening in the catheter which communicates with the lumen, and with the primary substrate extending through the radial opening with the at least one first electrically conductive element exposed exteriorly of the catheter. Preferably, the primary substrate is adapted to be wrapped around the catheter.

Additionally the invention provides a catheter having an elongated lumen extending from a proximal end, and a radial opening which communicates with the lumen, and comprising an assembly according to the invention, with the carrier means of the assembly extending through the lumen from the proximal end thereof, and with the primary substrate extending through the radial opening with the at least one first electrically conductive element exposed exteriorly of the catheter.

Further the invention provides a catheter having a lumen extending from a proximal end and a radial opening which communicates with the lumen, and comprising an elongated carrier means extending through the lumen from the proximal end thereof, and a primary substrate having at least one first electrically conductive element located thereon, the primary substrate extending from the carrier means through the radial opening with the at least one first electrically conductive element exposed exteriorly of the catheter.

In one embodiment of the invention the catheter is a balloon catheter comprising a balloon located on the catheter, the first electrically conductive elements being located on the catheter within the balloon. Preferably, the balloon is located on the catheter, with the catheter extending through the balloon, and defining with the balloon a hollow interior region extending around the catheter. Advantageously, the balloon is located adjacent the distal end of the catheter.

In an alternative embodiment of the invention the catheter is a plain catheter.

The advantages of the invention are many. Catheters produced by the method according to the invention can be produced relatively quickly and easily. The primary substrate with the first electrically conductive elements thereon can be produced separately of the catheter, and can either be produced integrally with the carrier means or attached to the carrier means to provide the assembly, which is also according to the invention. The assembly of the primary substrate with the first electrically conductive elements provided thereon and with the carrier means either integrally formed with the primary substrate or attached thereto can then be readily easily fed into and through the lumen of the catheter until the primary substrate is located adjacent a radial opening in the catheter, at which stage the primary substrate can be readily easily urged through the radial opening and attached to the catheter with the first electrically conductive elements exposed exteriorly of the catheter. This significantly increases the ease and simplicity with which a catheter can be produced.

By providing the carrier means in the form of a secondary substrate having second electrically conductive elements formed thereon which are either connected to or integrally formed with the first electrically conductive elements provides a further advantage in that the assembly of the primary and secondary substrates can be produced separately of the catheter, and there is no danger of the second electrically conductive elements being incorrectly connected to the first electrically conductive elements.

By providing the primary substrate of a resilient material, the primary substrate can be coiled around the carrier means, and when aligned with the radial opening can be urged through the radial opening by rotating the carrier means in the lumen. The resilience in the primary substrate results in the primary substrate winding itself around the outer surface of the catheter as it is being unwound from the carrier means and urged through the radial opening. Providing the secondary substrate as a resilient material which is coiled to form a roll has the additional advantage that the carrier means is relatively strong in torsion, thus facilitating rotating of the carrier means for urging the primary substrate outwardly through the radial opening.

The advantages of the catheter according to the invention and the advantages of the assembly for use in the manufacture of a catheter according to the invention are substantially similar to the advantages discussed above which are achieved by the method according to the invention.

BRIEF DESCRIPTION OF THE DRAWINGS

The invention will be more clearly understood from the following description of a preferred embodiment thereof, which is given by way of example only, with reference to the accompanying drawings, in which:

FIG. 2 is an enlarged transverse cross-sectional end elevational view of a portion of the balloon catheter of FIG. 1 on the line II-II of FIG. 1, FIG. 3 is a perspective view of a portion of the balloon catheter of FIG. 1 being formed by the method according to the invention, FIG. 4 is a side elevational view of an assembly also according to the invention for use in the manufacture of the balloon catheter of FIG. 1, FIG. 6 is an enlarged cross-sectional end view of the assembly of FIG. 4 on the line V-V of FIG. 4, FIG. 8 is a side elevational view of the assembly of FIG. 4 being formed.

DETAILED DESCRIPTION OF THE INVENTION

Figure 1:
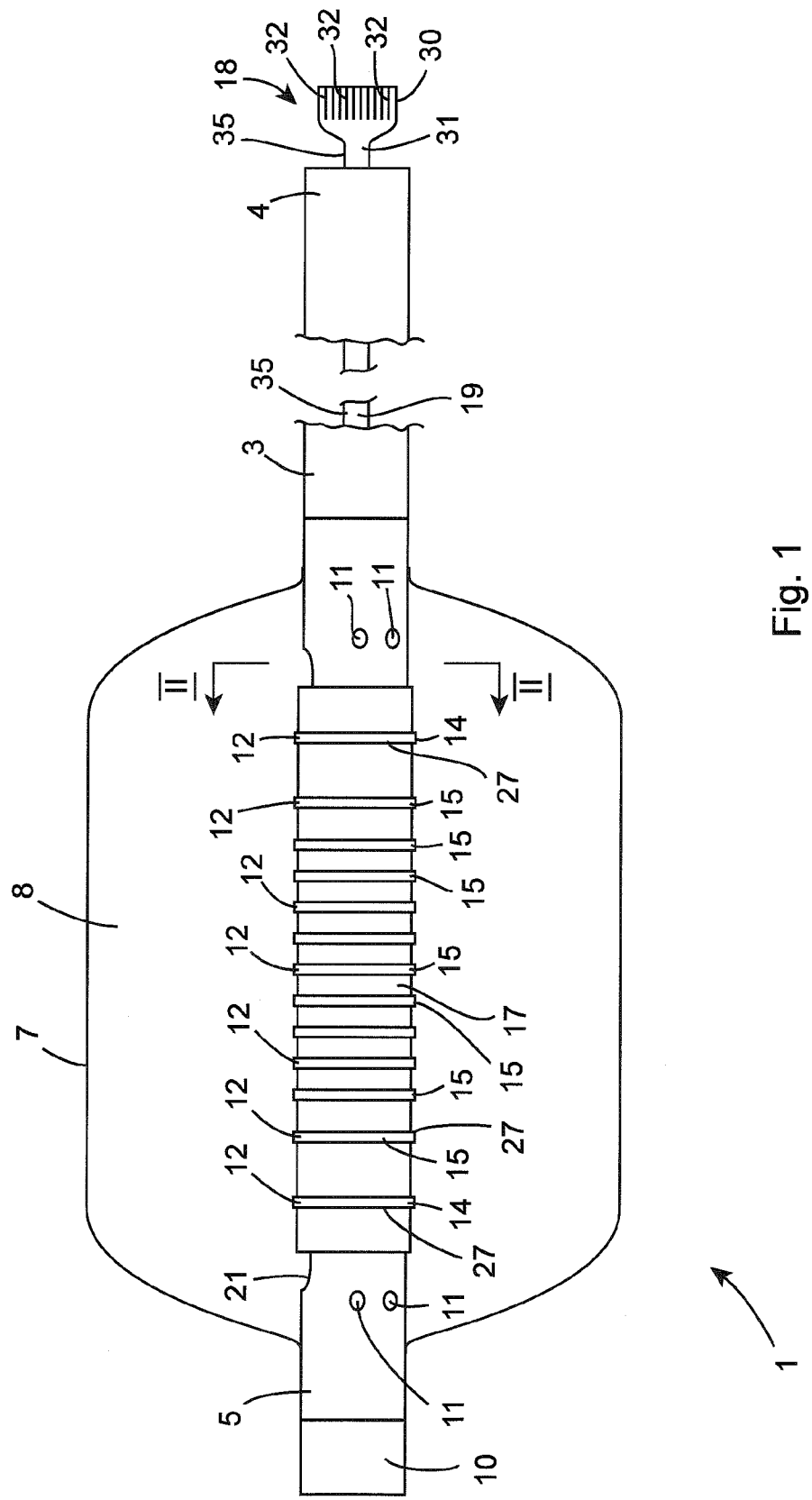
FIG. 1 is a side elevational view of a balloon catheter according to the invention having been manufactured by a method also according to the invention.

Referring to the drawings, there is illustrated a catheter according to the invention, which in this embodiment of the invention is a balloon catheter, indicated generally by the reference numeral 1. The balloon catheter 1 comprises an elongated catheter 3 extending from a proximal end 4 to a distal end 5. An inflatable element comprising a balloon 7 is located on the catheter 3 adjacent to but slightly spaced apart from the distal end 5 with the catheter 3 extending through the balloon 7 to define with the balloon 7 a hollow interior region 8, which extends around the catheter 3. A first lumen 9 extends through the catheter 3 from the proximal end 4 to the distal end 5 for accommodating an inflating medium for inflating the balloon 7, see FIGS. 2 and 3. An end cap 10 secured to the distal end 5 of the catheter 3 sealably closes the first lumen 9 adjacent the distal end 5 of the catheter 3. A plurality of radial ports 11 extending radially through the catheter 3 from the first lumen 9 accommodate the inflating medium from the first lumen 9 into the hollow interior region 8 of the balloon 7 for inflating thereof.

A plurality of longitudinally spaced apart and mutually electrically insulated first electrically conductive elements, namely, measuring electrodes 12, which are provided in the form of band electrodes extend around the catheter 3 within the balloon 7. The measuring electrodes 12 are provided for facilitating measuring of the transverse cross-sectional area and/or diameter of the balloon 7 adjacent the electrodes 12, as well as for determining the volume of the balloon 7. The measuring electrodes 12 comprise two spaced apart outermost stimulating electrodes 14 and a plurality of spaced apart sensing electrodes 15 which are located between and spaced apart from the stimulating electrodes 14. The sensing electrodes 15 each produce a voltage signal in response to a constant electric current being applied to the stimulating electrodes 15 when the balloon 7 is inflated with an electrically conductive medium, for example, a saline solution. The voltage response signal produced by each sensing electrode is indicative of the transverse cross-sectional area of the balloon 7 adjacent that sensing electrode 15. In this embodiment of the invention the balloon 7 is assumed to be of circular transverse cross-section when inflated, and thus, the voltage response signals produced on the sensing electrodes 15 are indicative of both the values of the transverse cross-sectional area and the diameter of the balloon 7 adjacent the corresponding sensing electrodes 15.

Such balloon catheters will be well known to those skilled in the art. A description of such balloon catheters is provided in PCT published Application Specification No. WO 2009/001328.

The measuring electrodes 12 are formed on a primary substrate 17 of an assembly, which is also according to the invention and indicated generally by the reference numeral 18, and as well as the primary substrate 17, the assembly 18 also comprises a carrier means, namely, an elongated secondary substrate 19 from which the primary substrate 17 extends. The assembly 18 is located in a second lumen 20 of the catheter 3 with the primary substrate 17 extending from the secondary substrate 19 through a radial opening, which is located intermediate the proximal end 4 and the distal end 5 of the catheter 3, and which in this case is provided by an elongated radial slot 21 extending radially through the catheter 3 from the second lumen 20 adjacent the distal end 5 of the catheter 3 within the balloon 7. The primary substrate 17 is wrapped around an outer surface 22 of the catheter 3, and is secured thereto as will be described below with the measuring electrodes 12 exposed exteriorly of the catheter 3 within the balloon 7. The second lumen 20 extends through the catheter 3 from the proximal end 4 to the distal end 5 thereof, and is sealably closed at the distal end 5 by the end cap 10.

In this embodiment of the invention the primary and secondary substrates 17 and 19 are integrally formed and are cut out from one single sheet of material, namely, a flexible membrane 25 of electrically insulating material. The membrane 25 is of polyimide material, and is relatively thin, in this embodiment of the invention the membrane 25 is of thickness of approximately 25 microns, although the membrane 25 may be of thickness up to 150 microns. The membrane 25 is also relatively resilient. The measuring electrodes 12 are formed on the primary substrate 17 by first electrically conductive tracks 27 which are formed onto the primary substrate 17 by a deposition process, in this case by metal sputtering. A plurality of spaced apart mutually electrically insulated second electrically conductive elements, which in this embodiment of the invention are provided by second electrically conductive tracks 28 are formed onto the secondary substrate 19 by a deposition process, which in this case is also by metal sputtering. The number of second electrically conductive tracks 28 is similar to the number of first electrically conductive tracks 27, and the first electrically conductive tracks 27 are connected to respective corresponding ones of the second electrically conductive tracks 28. Two of the second electrically conductive tracks 28 are connected to the two stimulating electrodes 14 for applying the constant electrical current to the stimulating electrodes 14. The remainder of the second electrically conductive tracks 28 are connected to corresponding ones of the sensing electrodes 15 for conducting the voltage response signals from the sensing electrodes 15. The second electrically conductive tracks 28 are formed on the secondary substrate 19 simultaneously with the first electrically conductive tracks 27 on the primary substrate 17 by the same metal sputtering process. The second electrically conductive tracks 28 terminate in a connecting means comprising an electrical connector 30 which is secured to the secondary substrate 19 at a proximal end 31 thereof for connecting to electronic control and analysing equipment (not shown). The electronic control and analysing equipment may be operated under the control of, for example, a personal computer for applying the constant current signal to the stimulating electrodes 14, and for reading the voltage response signals from the respective sensing electrodes 15, for in turn computing the transverse cross-sectional area and/or diameter of the balloon 7 adjacent the respective sensing electrodes 15 and the volume of the balloon 7.

Figure 7:
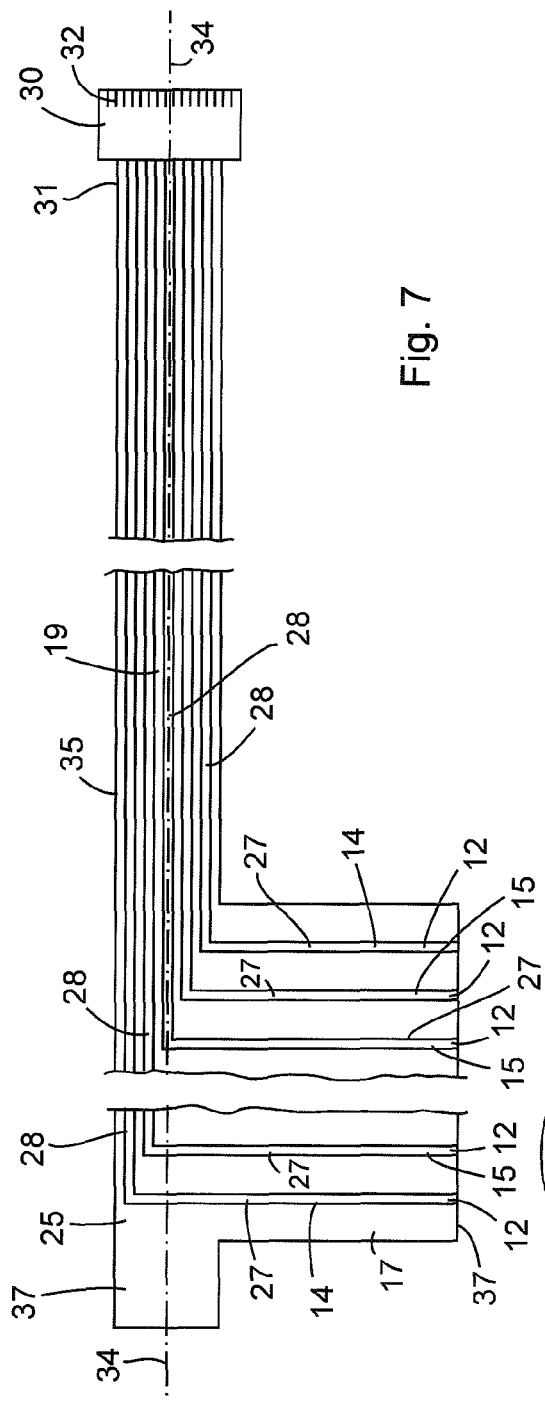
FIG. 7 is an enlarged developed plan view of the assembly of FIG. 4.

The assembly 18 is formed with the membrane 25 lying flat and planar as illustrated in FIG. 7. The first electrically conductive tracks 27 to form the measuring electrodes 12 and the second electrically conductive tracks 28, together with connecting tabs 32 of the electrical connector 30 are simultaneously formed by printing onto the membrane 25 by the metal sputtering process through a mask onto the membrane 25. Since the membrane 25 is of an electrically insulating material, the first electrically conductive tracks 27 are mutually electrically insulated from each other as are the secondary electrically conductive tracks 28 and the connecting tabs 32 also mutually electrically insulated from each other. The second electrically conductive tracks 28 are coated with an electrically insulating coating up to the point where they join the first electrically conductive tracks 27 which form the measuring electrodes 12.

Figure 5:
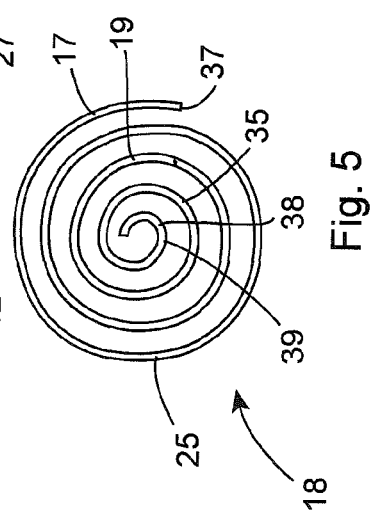
FIG. 5 is an enlarged end view of the assembly of FIG. 4 from one end.

After forming of the first and second electrically conductive tracks 27 and 28 and the electrically conductive tabs 32 onto the membrane 25, the part of the membrane 25 which forms the secondary substrate 19 is coiled around a longitudinally extending central axis 34 to form the secondary substrate 19 into an elongated carrier 35 in the form of a roll. On the secondary substrate 19 being formed into the carrier 35, the primary substrate 17 is coiled around the carrier 35, so that with the primary substrate 17 coiled around the carrier 35, the carrier 35 can be entered into and urged through the second lumen 20 of the catheter 3 from the proximal end until the primary substrate 17 is located adjacent the radial slot 21. Although in FIGS. 2, 5 and 6 the primary substrate 17 and the secondary substrate 19 are illustrated as being loosely coiled for the purpose of ease of illustration, the primary and secondary substrates 17 and 19 are tightly coiled as the carrier and the primary substrate 17 are being entered into the proximal end 4 of the second lumen 9, and are being urged through the second lumen 9.

With the carrier 35 located in the second lumen 20 and the primary substrate 17 located adjacent the radial slot 21, the proximal end 31 of the carrier 35 is gripped and rotated in the second lumen 20 in a direction corresponding to the rotational direction in which the secondary substrate 19 was rolled to form the carrier 35 until a longitudinally extending free edge 37 of the primary substrate 17 is aligned with the radial slot 21. The carrier 35 is then rotated in the opposite rotational direction in the second lumen 20 for unwinding the primary substrate 17 from the carrier 35 and urging the primary substrate 17 through the radial slot 21 and around the outer surface 22 of the catheter 3.

The inherent resilience of the membrane 25 is such that once the part of the membrane 25 which forms the secondary substrate 19 is coiled into the roll, and the primary substrate 17 is coiled around the secondary substrate 19, the secondary substrate 19 is retained in the roll by the inherent resilience of the membrane 25. Similarly, the primary substrate 17 is also retained wrapped around the carrier 35 by the inherent resilience of the membrane 25. Thus, when the portion of the membrane 25 which forms the primary substrate 17 is being unwound and urged through the radial slot 20, the inherent resilience of the membrane urges the primary substrate 17 to wrap itself around the catheter 3.

The primary substrate 17 is then secured to the outer surface 22 of the catheter 3 by bonding with an adhesive 36 with the first electrically conductive tracks 27 exposed to form the measuring electrodes 12 as band electrodes.

A distal portion 38 of the carrier 35 extends axially beyond the portion of the membrane 25 which forms the primary substrate 17 in order to form a stabilising element 39 for engaging the second lumen 20 distally beyond the radial slot 21 for stabilising the carrier 35 in the second lumen 20 to facilitate rotation of the carrier 35 in the second lumen 19.

Thereafter the balloon 7 is sealably secured to the catheter 3 with the radial ports 11 and the measuring electrodes 12 located within the balloon 7.

The second lumen 20 is sealed adjacent the proximal end of the catheter 3 with the proximal end 31 and the electrical connector 30 extending therefrom. A coupling element (not shown) is sealably secured to the proximal end 4 of the catheter 3 to communicate with the first lumen 9 for connecting the first lumen 9 to an inflating medium source (not shown).

To manufacture the balloon catheter 1, the catheter 3 is formed, typically by extrusion with the first and second lumens 9 and 20 extending longitudinally therethrough, and if required, further lumens may be formed during the extrusion of the catheter 3. The radial ports 11 are then formed by, for example, drilling through the catheter 3 into the first lumen 9. The elongated radial slot 21 is formed in the catheter 3 to communicate with the second lumen 20. The assembly 18 which is formed as already described is then entered into the second lumen 20 from the proximal end 4 of the catheter 3 with the stabilising portion 39 forming the leading end of the carrier 35. The carrier 35 is urged through the second lumen 20 until the primary substrate 17 is located adjacent the radial slot 21.

The carrier 35 is rotated in the second lumen 20 in the rotational direction in which the roll of the carrier 35 is formed until the longitudinal free edge 37 of the primary substrate 17 is aligned with the radial slot 21. The carrier 35 is then rotated in the reverse direction to unwind the primary substrate 17 from the carrier 35 and in turn to urge the primary substrate 17 through the radial slot 21, which in turn wraps itself around the outer surface 22 of the catheter 3 with the measuring electrodes 12 exposed exteriorly of the catheter 3. The primary substrate 17 is then bonded to the catheter 3 by the adhesive 36 with the measuring electrodes 12 exposed.

The proximal end 4 of the second lumen 20 is sealed with the carrier 35 sealably extending through the second lumen 20, and the distal ends 5 of the first and second lumens 9 and 20 are sealably closed by the end cap 10. Additionally, if desired, the second lumen 20 may be sealed at respective opposite ends of the radial slot 21.

The balloon 7 is then sealably secured to the catheter 3 adjacent the distal end 5 with the radial ports 11 and the measuring electrodes 12 located within the balloon 7.

If, instead of a balloon catheter, the catheter according to the invention is to be produced as a plain catheter without a balloon and with measuring electrodes formed as band or other electrodes adjacent the distal end of the catheter, the catheter according to the invention can be readily produced as a plain catheter by merely omitting the balloon 7 from the catheter 3.

It is also envisaged that instead of urging the assembly 18 of the carrier 35 and the primary substrate 17 with the measuring electrodes 12 thereon into the second lumen 20 from the proximal end 4 of the catheter 3 towards the distal end 5 of the catheter 3 until the primary substrate 17 is adjacent the radial slot 21, the assembly 18 may alternatively be urged through the second lumen by urging the proximal end of the carrier 35 into the second lumen 20 through the radial slot 21, and the carrier 35 would be urged through the second lumen 20 towards the proximal end 4 of the catheter 3 until the primary substrate 17 is located adjacent the radial slot 21. The portion of the primary substrate 17 adjacent the carrier 35 would be urged through the radial slot 21 into the second lumen 9, so that the primary substrate 17 would extend from the carrier 35 located within the second lumen 20 through the radial slot 21. The primary substrate 17 would then be wrapped around the outer surface 22 of the catheter 3, and would then be bonded to the outer surface 22 of the catheter 3 as already described.

It is envisaged that in cases where the assembly 18 is entered into the second lumen 20 through the radial slot 21, the electrical connector 30 would be connected to the proximal end of the carrier 35 and to the second electrically conductive tracks 28 after the assembly 18 had been urged through the second lumen 20 to the proximal end thereof.

While the catheter according to the invention has been described as comprising a balloon catheter, the catheter may be provided in the form of any other type of catheter, whether it be a plain catheter or a balloon catheter. It is also envisaged that the first electrically conductive tracks which form the measuring electrodes on the catheter may be provided for purposes other than for measuring values of a transverse cross-sectional dimension of a vessel or lumen in which the catheter is located. For example, it is envisaged that the first electrically conductive tracks may be provided for applying a current or a high frequency signal to tissue adjacent the first electrically conductive tracks for ablating the tissue.

It is also envisaged that instead of providing the first electrically Conductive tracks as electrodes, one or more of the first electrically conductive tracks may be provided in the form of an electrical resistive track to form one or more heating elements which may also be used for ablating tissue. In cases where the first electrically conductive tracks are provided as heating elements as opposed to electrodes, it is envisaged that each track would be coupled to a pair of the second electrically conductive tracks for providing a voltage across the first electrically conductive tracks.

Additionally, while the measuring electrodes have been described as being band electrodes, while it is desirable that the electrodes should extend completely around the catheter, it is not essential that the electrodes should extend completely around the catheter. Indeed, in certain cases, the electrodes could be provided as relatively small dot type electrodes, half band electrodes, quarter band electrodes or of any other suitable configuration extending only partly around the catheter. It is also envisaged that where the first electrically conductive tracks are provided in the form of electrically resistive heating elements, the first electrically conductive tracks may be provided in any suitable configuration, besides band configuration.

While the carrier means has been described as being provided by a secondary substrate in the form of a flexible resilient membrane suitable for facilitating forming the second electrically conductive tracks thereon by a metal sputtering process, it is envisaged that instead of the carrier means being provided as a flexible membrane, the carrier means may be provided in the form of a rigid or a semi-rigid substrate on which the second electrically conductive tracks would be formed by any suitable process. The primary substrate would then be secured to the rigid or semi-rigid substrate, for example, by adhesive bonding or the like, and the first and second electrically conductive tracks would be appropriately electrically connected.

It is also envisaged that the resilient membrane may be pre-tensioned to coil inwardly around and along the central axis to form the carrier in the form of a tightly formed roll, and to retain the carrier in the tightly formed roll. The portion of the membrane which forms the primary substrate would also be pre-tensioned to coil inwardly around the carrier, so that as the primary substrate is being unwound from the carrier and urged through the radial slot, the pre-tensioning in the primary substrate would inherently cause the primary substrate to coil tightly around the outer surface of the catheter, so that the primary substrate would be tightly secured to the catheter by its own inherent pre-tensioned resilience.

It is also envisaged that in certain cases, where the primary substrate is pre-tensioned to coil around the carrier, the pre-tensioning in the primary substrate could be such that when the primary substrate is urged outwardly through the radial slot to wrap around the outer surface of the catheter 3, the pre-tensioning of the primary substrate could be sufficient to retain the primary substrate securely attached to the catheter and extending around the catheter, without the need to bond the primary substrate to the outer surface of the catheter.

While the membrane which forms the primary and secondary substrates has been described as being formed of a flexible and resilient membrane, while it is desirable it is not essential that the membrane be of a resilient material. It is also envisaged that where the secondary substrate which forms the carrier means is of a rigid or semi-rigid substrate material, the primary substrate could be formed by the resilient material which could be pre-tensioned to coil around the secondary substrate.

It is also envisaged that the carrier means may be provided as a loom comprising a plurality of mutually electrically insulated electrically conductive wires. The primary substrate would then be suitably attached to the loom, and the wires in the loom would be suitably electrically connected to corresponding ones of the measuring electrodes by a suitable electrical coupling means, for example, by soldering or adhesive bonding or other suitable wire bonding techniques.

It is also envisaged that where the carrier means is provided by a loom comprising a plurality of mutually electrically insulated electrically conductive wires, the primary substrate may be provided by a resilient or a resilient pre-tensioned membrane pre-tensioned to coil inwardly around the wire loom, so that when urged outwardly through the radial slot, the pre-tensioned resilient primary substrate would wrap around the outer surface of the catheter and would be secured thereto by the inherent pre-tensioned resilience of the primary substrate.

While the primary substrate has been described as being coiled around the catheter, in certain cases, it is envisaged that the primary substrate may merely extend through the slot and would be bonded to the catheter adjacent the slot. In which case, the primary substrate would not extend around the catheter, and in such a case, the first electrically conductive elements would form relatively short electrodes or electrically resistive heating elements.

While it is advantageous, it is not essential that the primary substrate should extend completely around the catheter.

While the first and second electrically conductive tracks have been described as being formed onto a membrane by a deposition process, such as metal sputtering, it is envisaged that the first and second electrically conductive tracks could be printed onto the membrane. It is also envisaged that in certain cases the first and second electrically conductive tracks may be etched from an electrically conductive foil which would be laminated onto the membrane.

Additionally, while the membrane has been described as comprising a single sheet of material, in certain cases, it is envisaged that the membrane may be formed from a compound sheet whereby a plurality of laminates of similar or different materials would be laminated together by bonding or any other suitable laminating means to form the single sheet. In such cases, it is envisaged that one of the layers of the compound sheet may be an electrically conductive layer, which would be etched to form the first and second electrically conductive tracks, in a similar manner as a printed circuit board is formed.

While the balloon catheter has been described as comprising a plurality of sensing electrodes, it is envisaged that in certain cases one single sensing electrode may be sufficient, depending on the size of the balloon, and the use to which the balloon catheter is being put. It is also envisaged in certain cases that a single stimulating electrode may be sufficient.

It is also envisaged that in certain cases a stiffening means, such as an elongated stiffening element, for example, a relatively stiff wire, may be provided for stiffening the carrier means, to assist urging the carrier means through the lumen. In the embodiment of the invention whereby the carrier is formed by rolling a secondary substrate to form a roll, the stiffening element could be provided such that the secondary substrate would be wound around the stiffening element. Similarly, in an embodiment of the invention where the carrier is provided by a loom of wires, it is envisaged that the stiffening element could extend longitudinally, for example, centrally through the loom. The stiffening element could be located such that it could remain a permanent fixture in the catheter, or it could be removed subsequent to locating the assembly in the catheter with the primary substrate extending through the radial opening.

Balloon catheters and plain catheters according to the invention and manufactured according to the method of the invention are suitable for use in many medical and surgical applications, for example, determining the volume or transverse cross-sectional area and/or diameter of a vessel, lumen or organ of the human or animal body, for example, a blood vessel, a cavity of the heart, the stomach, the urethra, the oesophagus, the intestine and other such vessels, lumens and organs. Balloon catheters and plain catheters according to the invention and manufactured according to the method of the invention are also suitable for ablating tissue in a vessel, lumen or organ in a human or animal body.

The invention claimed is:

1. A method for manufacturing a catheter, the method comprising:
   providing a catheter with an elongated lumen extending through the catheter from a proximal end thereof, and a radial opening communicating with the lumen,
   providing a primary substrate having at least one first electrically conductive element located thereon with the primary substrate extending from an elongated carrier means,
   wrapping the primary substrate around the carrier means,
   urging the carrier means with the primary substrate wrapped around the carrier means through the lumen of the catheter from the proximal end thereof until the primary substrate is located adjacent the radial opening,
   urging the primary substrate through the radial opening, and
   wrapping the primary substrate around the catheter with the at least one first electrically conductive element exposed exteriorly of the catheter.

2. A method as claimed in claim 1 in which the primary substrate is secured on an outer surface of the catheter.

3. A method as claimed in claim 1 in which the primary substrate comprises a resilient material, and is pre-tensioned to coil inwardly to wrap around the catheter.

4. A method as claimed in claim 1 in which the primary substrate is unwound from the carrier means as the primary substrate is being urged through the radial opening in the catheter.

5. A method as claimed in claim 1 in which the primary substrate is located on the catheter adjacent the distal end thereof, and each first electrically conductive element forms one of an electrode and an electrically resistive heating element.

6. A method as claimed in claim 1 in which the primary substrate is secured to the outer surface of the catheter by bonding.

7. A method as claimed in claim 1 in which the primary substrate and the at least one first electrically conductive element extends at least partially around the catheter.

8. A method as claimed in claim 1 in which the primary substrate is unwound from the carrier means by rotating the carrier means in the lumen.

9. A method as claimed in claim 1 in which the at least one first electrically conductive element is formed by an electrically conductive track formed on the primary substrate.

10. A method as claimed in claim 1 in which the primary substrate comprises a membrane of an electrically insulating material.

11. A method as claimed in claim 1 in which the carrier means comprises at least one second electrically conductive element electrically connected to a corresponding one of the at least one first electrically conductive element on the primary substrate.

12. A method as claimed in claim 11 in which the carrier means comprises a secondary substrate, and the at least one second electrically conductive element is formed by an electrically conductive track extending longitudinally along the secondary substrate.

13. A method as claimed in claim 12 in which the secondary substrate comprises a membrane of an electrically insulating material.

14. A method as claimed in claim 12 in which the primary and secondary substrates are of similar material, and are integrally formed in one piece from the same sheet of material.

15. A method as claimed in claim 12 in which a plurality of first electrically conductive elements are provided on the primary substrate spaced apart and mutually electrically insulated from each other, and a plurality of the second electrically conductive elements are provided on the secondary substrate mutually electrically insulated from each other, the second electrically conductive elements being electrically connected to corresponding ones of the first electrically conductive elements.

16. A method as claimed in claim 12 in which the secondary substrate comprises an elongated substrate of resilient material defining an elongated longitudinally extending central axis, and being coiled about the central axis to form an elongated roll.

17. A method as claimed in claim 16 in which the secondary substrate is pre-tensioned to coil around the central axis.

* * * * *